United States Patent [19]

Launay et al.

[11] Patent Number: 5,241,607
[45] Date of Patent: Aug. 31, 1993

[54] METHOD FOR AUTOMATICALLY MATCHING SERIAL CROSS-SECTIONS OBSERVED WITH A MICROSCOPE

[76] Inventors: Didier M. Launay, 2 ter rue de la Roche-Jacquelein, F-78100 Saint Germain en Laye, France; Christophe R. Bron, Im Tobelacker 11, CH-8044 Zurich, Switzerland

[21] Appl. No.: 646,629

[22] PCT Filed: Jul. 21, 1989

[86] PCT No.: PCT/FR89/00396
§ 371 Date: Jan. 25, 1991
§ 102(e) Date: Jan. 25, 1991

[87] PCT Pub. No.: WO90/01197
PCT Pub. Date: Feb. 8, 1990

[30] Foreign Application Priority Data

Jul. 27, 1988 [CH] Switzerland ............... 2860/88-0

[51] Int. Cl.⁵ .................................. G06K 9/00
[52] U.S. Cl. ........................... 382/6; 382/1; 364/413.15
[58] Field of Search .................... 382/6, 1, 48; 364/413.13, 413.14, 413.15

[56] References Cited

U.S. PATENT DOCUMENTS 4,404,684  9/1983  Takada .................. 382/25
4,975,973  12/1990 Kasano et al. ........... 382/28

FOREIGN PATENT DOCUMENTS 2046940  2/1980  United Kingdom .

OTHER PUBLICATIONS

Bron et al "Three-Dimensional Electron Microscopy of Entire Cells", Journal of Microscopy, vol. 157, Pt. 1, Jan. 1990, pp. 115-126.

Primary Examiner—Michael T. Razavi
Assistant Examiner—Yon J. Couso
Attorney, Agent, or Firm—Pearne, Gordon, McCoy & Granger

[57] ABSTRACT

Three holes in known relative positions are made in a sample to be examined. After the sample has been serially cross-sectioned, the sections are imaged. Movement and deformation of each section is determined by comparing the positions of the holes in the sections to that of the original known relative positions. Based on the changes, an inverse transformation is determined and applied to the section image. The transformed images then provide serial cross sectional images of the sample without the degradation produced by the sectioning and imaging process.

8 Claims, 4 Drawing Sheets

MAGNIFICATION X 36000

MAGNIFICATION X 21000

MAGNIFICATION X 21000

METHOD FOR AUTOMATICALLY MATCHING SERIAL CROSS-SECTIONS OBSERVED WITH A MICROSCOPE

BACKGROUND OF THE INVENTION

This invention concerns a process that makes it possible to automate the calculation of deformations that make possible the matching of successive sections of microscopy, electronic transmission microscopy and optical microscopy.

The matching of successive sections is traditionally done by moving images according to the operator's judgment. This method does not make it possible to correct the deformations that the mechanical action of the cutting introduces to the thin sections.

Some deformations are related to the techniques used to make it possible to visualize successive sections in microscopy. These include Translation and rotation related to:
  placement of the sections one after the other within the grids or supporting blades which cannot be reproduced exactly, and
  deformations related to the mechanical actions of the microtome or the ultramicrotome.
Also included is
Systematic rotation related to different powers of enlargement (in the case of an electron microscope in transmission mode).

SUMMARY OF THE INVENTION

The process of the invention makes it possible to correct all these deformations by calculating an inverse transformation function and establishing a fixed marker derived from markings previously obtained mechanically or by firing a pulsed laser.

The process according to the invention takes place after the histological preparation stage, prior to observation with the optical microscope or the electron transmission microscope.

DETAILED DESCRIPTION OF THE PREFERRED EMBODIMENT

Figure 1:
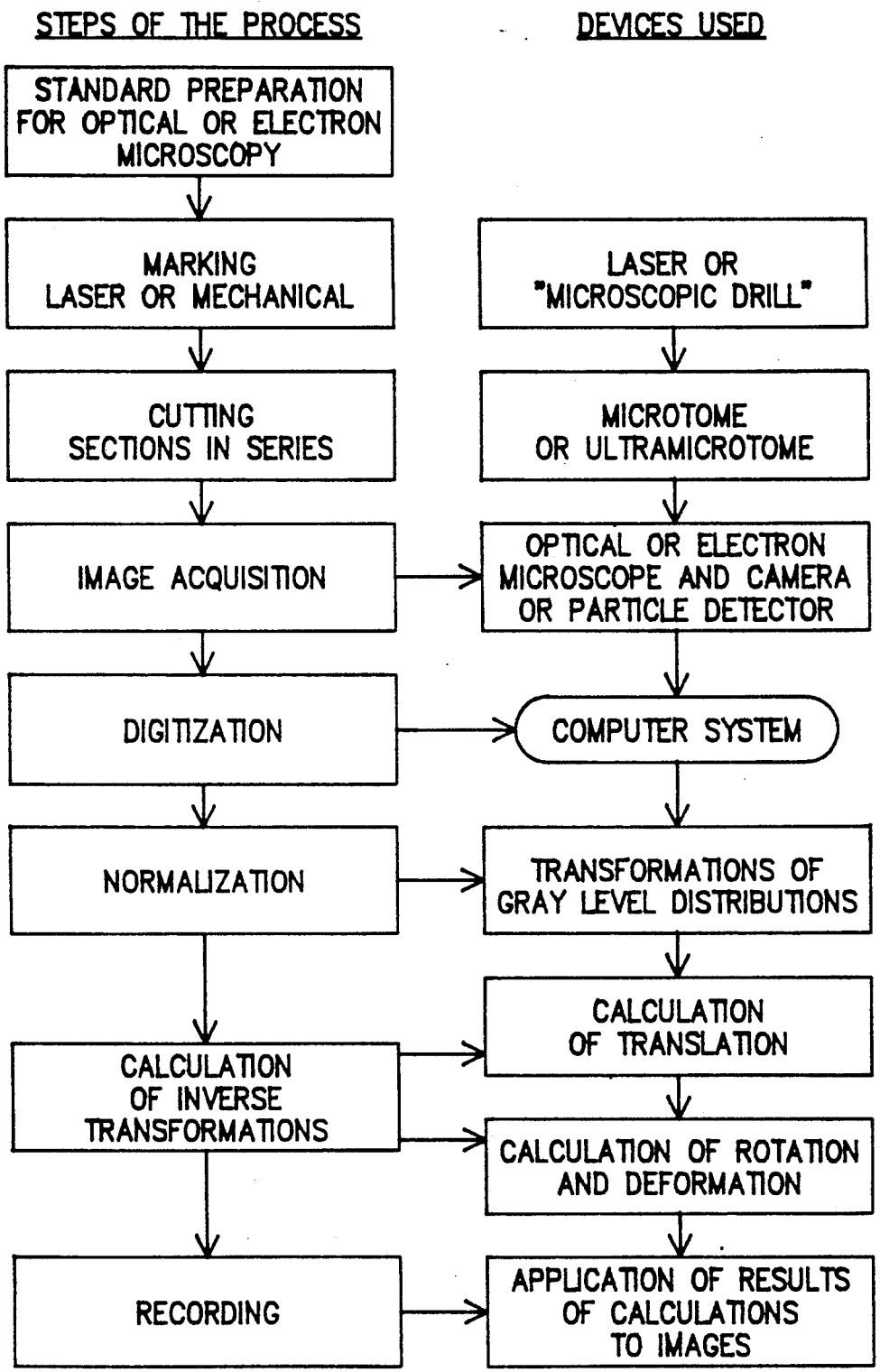
FIG. 1 is a block diagram of a process according to the invention.

The process according to the invention includes several steps: (See FIG. 1)

1. "Marking"

Figure 2:
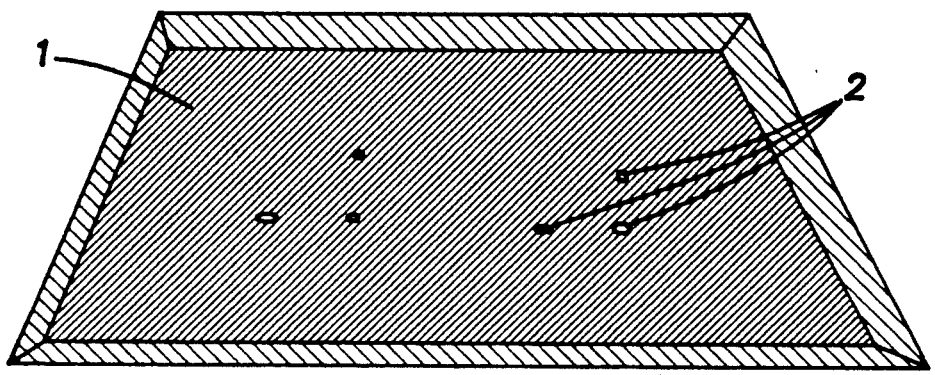
FIG. 2 is a perspective view of marking holes in a microscopic preparation (weak magnification).

The process according to the invention includes a sample preparation step before a series of sections is cut (see FIG. 2). The microscopic preparation 1 is pierced by at least three holes 2 not in a straight line near area to be studied and made either mechanically or by means of a pulsed laser. The barycenters of these holes 2 will be used as marking points to establish a fixed marker and for final calculation of the inverse transformation function.

2. "Section in Series"

Figure 3:
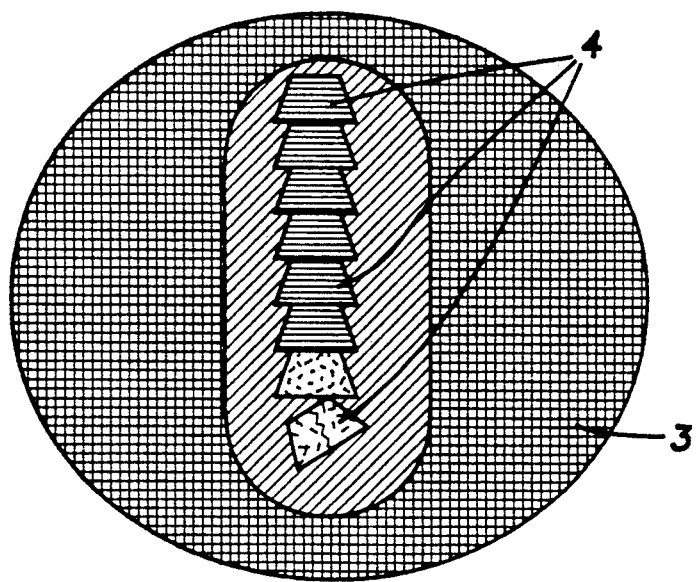
FIG. 3 is a plan view of an example of an electron microscope grid with a series of sections.

The process according to the invention takes the classic step of making successive sections 4 of the preparation 1 using a microtome for the sections to be viewed by optical microscopy and an ultramicrotome for sections to be viewed with an electron microscope (see FIG. 3).

3. Digitation

Figure 4A:
FIGS. 4A–4C are schematic drawings of the acquisition of images and rotation related to the functioning of an electronic transmission microscope between two different magnifications.
Figure 4B:
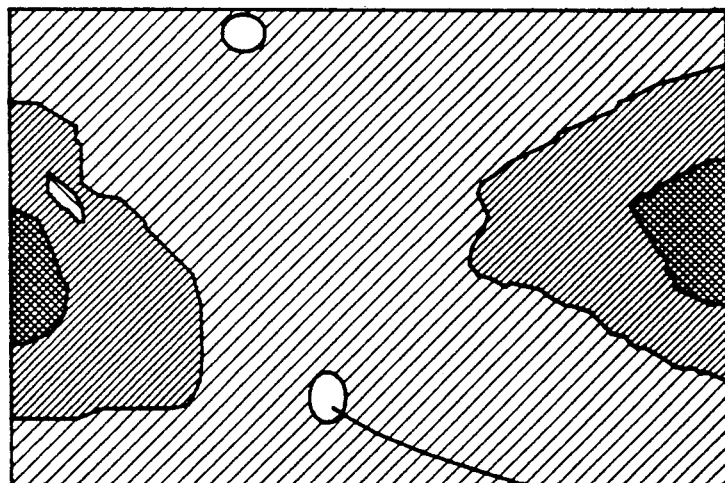
Figure 4C:
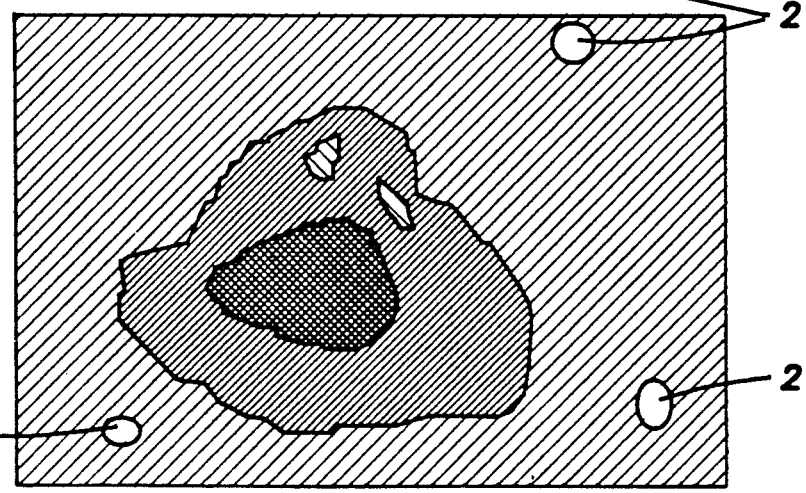

The process according to the invention includes observation steps with the optical microscope or with the electron transmission microscope, as well as the acquisition and digitation of images by a computer system. This computerized system includes a camera and an image-digitation system connected to a computer. Three images are acquired for an image to be studied (see FIG. 4):

Image A: The image that is going to be studied.
Image B: An image obtained at a weaker magnification, without moving the slide 3 making it possible to see at least one of the marking holes 2.
Image C: An image making it possible to visualize all the marking holes 2, at the same magnification as for image B.

4. "Normalization"

A normalization step for digital processing of all the images A of the sections to be studied, making it possible to obtain homogeneous information in terms of contrast and distribution of grey levels.

The distributions of the grey levels of the images are normalized in terms of their average and their variance.

Enhancement is done by dispersion of the diagram distributions.

Specific mathematical functions are used for the work on the distributions (improvement and stabilization).

5. "Calculation of the Inverse Transformation"

The process according to the invention includes a step for calculating the inverse transformation function making it possible to re-establish more closely from an initial section considered a reference a set marker that is fixed for all the sections. This method is as follows:

5.1 Automatic calculation of the translation between images B and C, which includes:
  5.1.1 Automatic detection of holes 2 by image-analysis methods (thresholding) on images B and C.
  5.1.2 Calculation of the barycenters of the holes 2 of image C.
  5.1.3 Calculation of the barycenters of the hole or holes 2 of image B.
  5.1.4 Superposition of the corresponding barycenters.
  5.1.5 Calculation of the translation necessary between the two images by calculating the distance of the two barycenters on the respective images.

Figure 5A:
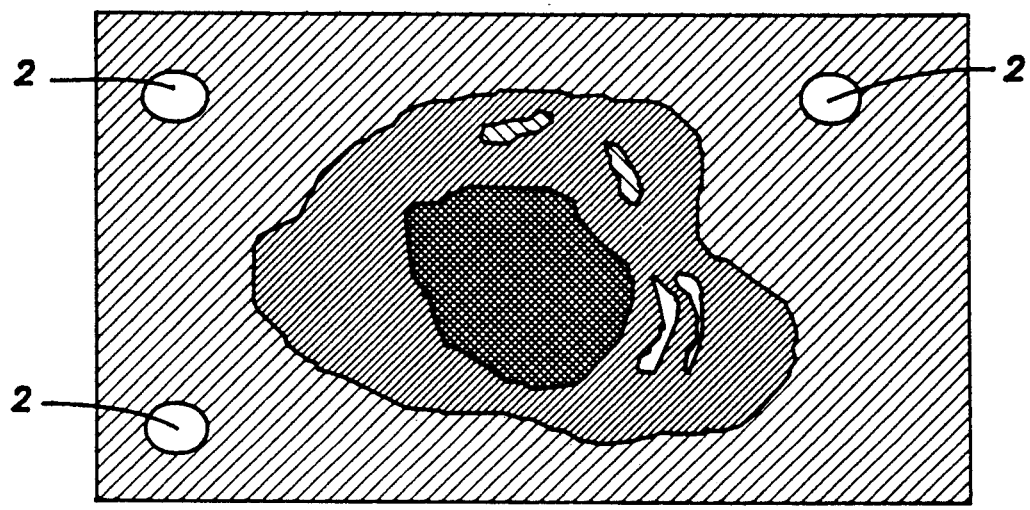
FIGS. 5A–5B are schematic drawings of deformations related to sectioning techniques.
Figure 5B:
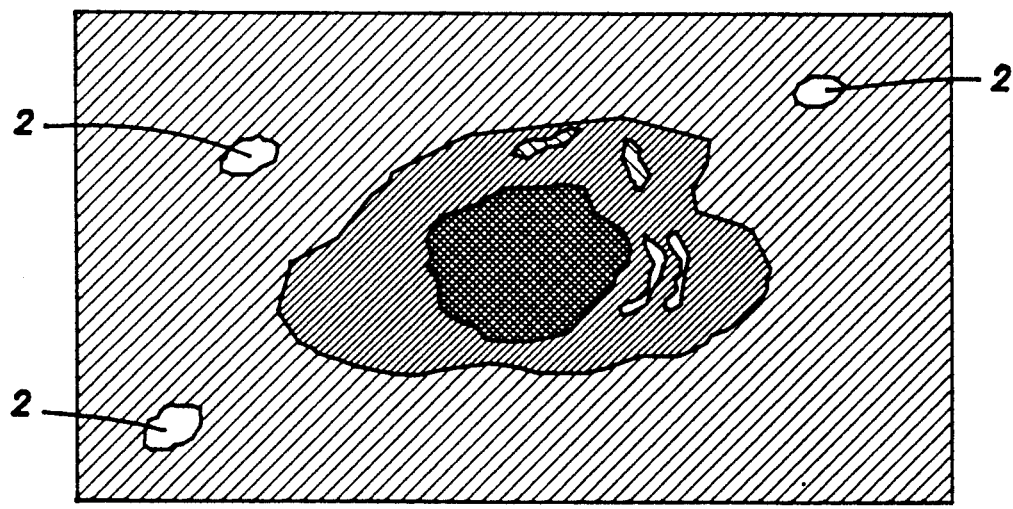

5.2 Calculation of Rotation and Deformation (See FIG. 5)

These two functions are to be applied to the image A in relation to the corresponding image of the preceding specimen section. They make possible virtual automatic recording of the series of images A.

5.2.1 Calculation of Rotation

The rotation is calculated by the angular sum of rotation related to the functioning of the specific apparatus at each magnification and of the rotation related to the random orientation of the section on the slide 3 of the microscope. The function related to the apparatus is given in advance; that of the position of the section is calculated on the basis of the orientation of the holes 2 in the image C.

5.2.2 Calculation of the Deformation

Knowing the position of the holes 2 before the section and their respective distances, calculation of the inverse deformation to be applied to the successive images in order to record the holes 2 and consequently the images that are coordinated with them uses a matrix model already tested in prior phases which up to now remains sufficient, namely:

an affine transformation of the first order with 6 parameters.

6. "Recording"

An image-recording step is obtained by digital processing applying to the images A the series of transformation functions as well as the rotations and translations calculated by the process in the invention described in the preceding step 5.

The process according to the invention is particularly adapted to the reconstruction of the information in three dimensions from successive sections 4 observed with the electron transmission microscope or an optical microscope. The information can then be used by employing digital image-processing techniques.

The process according to the invention makes it possible to automate the search for areas of one section on another within successive sections observed with the help of electron transmission microscopes whose movements of the microscope stage and control parameters are computer-controlled.

Moreover, the process according to the invention makes is possible to automate the search for areas of one section on another within successive sections observed with the aid of optical microscopes whose movements of microscope stage and control parameters are computer-controlled.

We claim:

1. A process for automating the matching of successive sections of a specimen to be microscopically observed, the process comprising:
    providing a marking means;
    using the marking means to mark the specimen with at least three holes in known relative positions proximate to an area to be studied;
    providing a specimen sectioning means;
    using the specimen sectioning means to section said specimen into a plurality of sections;
    creating at least three images of each section, a first image being of the area to be studied, a second image being at a weaker magnification than the first image and including same and at least one of the three holes, and a third image being at the same magnification as the second image and including all of the holes;
    digitizing said at least three images;
    calculating a barycenter for each hole included in said second and third images;
    calculating the relative positions of the barycenters for the holes of the third image;
    calculating an inverse transformation function from said known relative positions proximate to the area to be studied and said calculated relative positions;
    normalizing each section first image in contrast and grey level distribution;
    applying respective inverse transformation functions to each section first image to produce a corrected image for each section; and
    producing matched images of the successive sections from said corrected images.

2. A process according to claim 1, further comprising using said matched images to direct a microscopic imaging device to examine a particular area of successive sections.

3. A method according to claim 1, wherein the marking means comprises a laser.

4. A method according to claim 3, wherein the specimen sectioning means comprises a microtome.

5. A method according to claim 3, wherein the specimen sectioning means comprises an ultramicrotome.

6. A method according to claim 2, wherein the marking means comprises a laser.

7. A method according to claim 5, wherein the specimen sectioning means comprises a microtome.

8. A method according to claim 3, wherein the specimen sectioning means comprises an ultramicrotome.

* * * * *